United States Patent [19]
Jones

[11] Patent Number: 6,123,709
[45] Date of Patent: Sep. 26, 2000

[54] BONE BUTTRESS PLATE AND METHOD OF USING SAME

[76] Inventor: Andrew R. Jones, 216 Winsome La., Chapel Hill, N.C. 27516-4701

[21] Appl. No.: 08/900,330

[22] Filed: Jul. 25, 1997

[51] Int. Cl.$^7$ .................................................. A61B 17/56
[52] U.S. Cl. ................................ 606/69; 606/70; 606/71
[58] Field of Search .............................. 606/69, 70, 71, 606/61, 60, 72, 73, 96, 86

[56] References Cited

U.S. PATENT DOCUMENTS

| | | |
|---|---|---|
| 3,695,259 | 10/1972 | Yost . |
| 3,741,205 | 6/1973 | Markolf et al. . |
| 4,219,015 | 8/1980 | Steinemann ............................... 606/69 |
| 4,364,382 | 12/1982 | Mennen . |
| 4,403,606 | 9/1983 | Woo et al. . |
| 4,403,607 | 9/1983 | Woo et al. . |
| 4,454,876 | 6/1984 | Mears . |
| 4,573,458 | 3/1986 | Lower . |
| 4,683,878 | 8/1987 | Carter . |
| 4,773,406 | 9/1988 | Spector et al. . |
| 4,784,127 | 11/1988 | Mattheck et al. . |
| 4,800,874 | 1/1989 | David et al. . |
| 4,838,252 | 6/1989 | Klaue . |
| 4,867,144 | 9/1989 | Karas et al. ............................... 606/69 |
| 4,905,679 | 3/1990 | Morgan . |
| 4,923,471 | 5/1990 | Morgan .................................... 623/16 |
| 4,943,292 | 7/1990 | Foux . |
| 4,959,065 | 9/1990 | Arnett et al. . |
| 4,978,349 | 12/1990 | Frigg . |
| 5,002,544 | 3/1991 | Klaue et al. . |
| 5,015,248 | 5/1991 | Burstein et al. . |
| 5,053,036 | 10/1991 | Perren et al. . |
| 5,085,660 | 2/1992 | Lin . |
| 5,087,259 | 2/1992 | Krenkel . |
| 5,108,397 | 4/1992 | White . |
| 5,133,718 | 7/1992 | Mao . |
| 5,139,497 | 8/1992 | Tilghman et al. ........................ 606/69 |
| 5,147,367 | 9/1992 | Ellis . |

(List continued on next page.)

OTHER PUBLICATIONS

Leung et al., *Operative Treatment of Displaced Intra–Articular Fractures of the Calcaneum*, 75–B The Jour Bone and Joint Surgery, (Mar. 1993) pp. 196–201.

Eastwood et al., *Intra–Articular Fractures of the Calcaneum*, 75–B The Journal of Bone and Joint Surgery, (Mar. 1994) pp. 183–195.

O'Farrell et al., *Fractures of the os calcis: improved results with internal fixation*, Injury (1993) 24, pp. 263–265.

Crosby et al., *Open Reduction and Internal Fixation of Type II Intra–Articular Calcaneus Fractures*, Foot & Ankle International (May 1995) pp. 253–258.

Synthes USA Literature—Calcaneal Plates, No. 93–10, Jul. 16, 1993.

Synthes USA Literature—Calcaneal Y–Plates, No. 93–11, Jul. 19, 1993.

*Primary Examiner*—Michael Buiz
*Assistant Examiner*—Len Ngo
*Attorney, Agent, or Firm*—William A. Barrett; Steven J. Hultquist

[57] ABSTRACT

A bone buttress plate and a method of using the same to fixate a lateral surface of a fractured hindfoot calcaneus. The plate includes a main body, a first and a second leg, and an extension member. Each leg attaches to and extends from the main body. The extension member includes a yoke, a first arm, and a second arm. The yoke attaches to the main body and extends from the main body opposite to the legs. Each arm attaches to and extends from the yoke. The invention further includes a surgical method of fixating a fractured calcaneus exposed in a surgical theater, which includes providing a bone buttress plate including a main body, a first and a second leg, and an extension member. Each leg attaches to and extends from the main body. The extension member includes a yoke, a first arm, and a second arm. The yoke attaches to the main body and extends from the main body opposite to the legs. Each arm attaches to and extends from the yoke. The method then includes shaping the plate from a substantially planar configuration to an extent required for conformity to a lateral surface of the fractured calcaneus. The plate is then secured with mechanical fasteners to the fractured calcaneus, each mechanical fastener retentionally engaged with said bone buttress plate and an underlying region of the fractured calcaneus.

44 Claims, 6 Drawing Sheets

U.S. PATENT DOCUMENTS

| | | |
|---|---|---|
| 5,151,103 | 9/1992 | Tepic et al. . |
| 5,171,279 | 12/1992 | Mathews . |
| 5,197,966 | 3/1993 | Sommerkamp .......................... 606/69 |
| 5,201,733 | 4/1993 | Etheredge, III . |
| 5,201,737 | 4/1993 | Leibinger et al. ....................... 606/69 |
| 5,250,048 | 10/1993 | Gundolf . |
| 5,304,180 | 4/1994 | Slocum . |
| 5,324,291 | 6/1994 | Ries et al. . |
| 5,336,224 | 8/1994 | Selman . |
| 5,346,492 | 9/1994 | Morgan ...................... 606/60 |
| 5,364,398 | 11/1994 | Chapman et al. ....................... 606/69 |
| 5,372,598 | 12/1994 | Luhr et al. .............................. 606/69 |
| 5,468,242 | 11/1995 | Reisberg .................................. 606/69 |
| 5,487,741 | 1/1996 | Maruyama et al. . |
| 5,501,684 | 3/1996 | Schlapfer et al. . |
| 5,569,250 | 10/1996 | Sarver et al. ............................ 606/69 |
| 5,578,034 | 11/1996 | Estes . |
| 5,586,985 | 12/1996 | Putman et al. .......................... 606/69 |
| 5,690,631 | 11/1997 | Duncan et al. .......................... 606/69 |

BONE BUTTRESS PLATE AND METHOD OF USING SAME

BACKGROUND OF THE INVENTION

1. Field of the Invention

This invention relates to an internal bone buttress plate and, more particularly, to a bone buttress plate for fixating a fractured hindfoot and a method of using the same.

2. Description of the Related Art

Displaced intra-particular fractures of the calcaneus, or calcaneum, are one of the most disabling of fractures. A crushed calcaneum often divides into a number of fragments with one or more fragments displacing from their original positions. The fragmented and disorganized calcaneum loses its height and begins to bulge. As the calcaneus bulges, the heel broadens. The longitudinal arch in the foot is lost and the Achilles tendon lengthens. A longer Achilles tendon causes excessive upward flexion in the foot. The initial pain and swelling rarely diminish after the fracture has healed, and later problems develop due to scarring of the nerves, tendons, and muscles. If the calcaneum is permitted to heal in this deformed condition, the function of the foot is rendered nearly useless.

Orthopedic surgeons have begun using open reduction and internal plate fixation to restore a displaced and fragmented calcaneus. Leung et al. discuss buttressing the lateral wall of the calcaneum with plates designed for cervical applications [Operative Treatment of Displaced Intra-Articular Fractures of the Calcaneum, 75-B The Journal of Bone and Joint Surgery, 196 (March 1993)]. Eastwood et al. use a common 3.5 mm "Y" shaped reconstruction plate to stabilize a three-fragment calcaneus [Intra-Articular Fractures of the Calcaneum, 75-B The Journal of Bone and Joint Surgery, 189, 192 (March 1993)]. O'Farrell et al. show a common strip plate contoured to the shape of the calcaneus lateral wall to stabilize lateral wall fragments [Fractures of the os calis. improved results with internal fixation, 24 Injury 263 (1993)]. Crosby et al. use a common "H" plate to restore a two-fragment intra-articular calcaneus fracture [Open Reduction and Internal Fixation of Type II Intra-Articular Calcaneus Fractures, 17 Foot & Ankle International 253, 254 (May 1996)]. Though the above plates may have functioned satisfactorily in two- and three-fragment fractures, the procedures often required the use of additional pins, screws, and K-wires, and surgeons have also had to add bone graft to support a central articular fragment. Since the calcaneus can fracture into four or more fragments, a fixation plate designed specifically for the possible fracture patterns of the calcaneum, without the need for bone graft or additional pins, screws, or wires, is required.

In another publication Kerr et al. discuss early operative results using a specialized AO calcaneal fracture plate [AO Calcaneal Fracture Plate, 27 Injury: International Journal of the Care of the Injured, 39 (1996)]. Though this plate was designed for calcaneal fractures, the plate itself is structurally weak and has been known to fracture when subjected to the plantarward forces of the foot while the patient is walking. Since the lateral cortex of the calcaneus is always severely comminuted, screw fixation of the central fragment is also complicated and the plate design causes the bone screws to anchor into mushy bone fragments. A further complication with this plate design is "blindly" anchoring bone screws into the sustentaculum from a lateral approach. This "blind" procedure places the adjacent neurovascular structures at risk.

There is, accordingly, a need in the art for a bone plate specifically designed for restoration of a severely displaced calcaneus, a plate design which could replace the need for bone grafting, a plate designed to provide a firm anchor for mechanical fasteners passing through the severely comminuted calcaneus lateral cortex, and a plate design which is structurally sound to withstand the plantarward forces imparted during walking.

It is, therefore, an object of the present invention to provide an internal bone buttress plate capable of withstanding the plantarward forces imparted on the plate while the patient is walking.

It is another object of the present invention to provide an internal bone buttress plate designed to minimize the need for additional pins, screws, or wires when restoring a severely displaced calcaneus.

It is another object of the present invention to provide an internal bone buttress plate designed to reduce the need for bone grafting.

It is another object of the present invention to provide an internal bone buttress plate designed to bridge a severely comminuted calcaneus lateral cortex and to provide a solid anchor for mechanical fasteners into the sustentacular region.

It is another object of the present invention to provide an internal bone buttress plate designed to secure mechanical fasteners into the sustentacular region without risking adjacent neurovascular structures.

It is another object of the present invention to provide an internal bone buttress plate designed to improve fixation to a large body fragment and to an anteromedial fragment.

Other objects and advantages of the present invention will be more fully apparent from the ensuing disclosure and appended claims.

SUMMARY OF THE INVENTION

The aforementioned problems are resolved by a bone buttress plate including a main body, a first and a second leg, and an extension member. Each leg attaches to and extends from the main body. The extension member includes a yoke, a first arm, and a second arm. The yoke attaches to the main body and extends from the main body opposite to the legs. Each arm attaches to and extends from the yoke.

One aspect of the invention advantageously includes a top surface and a bone application surface opposite the top surface, with the main body, legs, yoke, and arms each including at least one opening extending from the top surface to the bone application surface for attachment to a bone.

In another aspect of the invention the main body beneficially includes at least one generally oval opening extending from the top surface to the bone application surface for attachment to the bone.

The invention may include an embodiment wherein each opening and each generally oval opening includes a countersink on the top surface and a countersink on the bone application surface.

The plate may further include embodiments wherein the main body is generally cruciform shaped or generally rectangular shaped.

In a further aspect of the invention the plate is made of a thin malleable biocompatible material.

The bone buttress plate of the present invention has several advantages over the prior art. Since the main body is designed to withstand the plantarward forces imparted on the plate while the patient is walking, the plate thus solves the fracture problems of the prior art. The main body is also designed to bridge a severely comminuted calcaneus lateral cortex. The design of the main body thus eliminates bone screws anchoring into mushy bone fragments and provides a solid anchor for mechanical fasteners into the sustentacular region. The design of the plate further ensures the large body fragment and the anteromedial fragment are each firmly secured at two points. The plate thus improves upon the prior art and provides improved fixation to a large body fragment and to an anteromedial fragment.

Since the plate is specifically designed for the possible fracture patterns of a calcaneus, the plate is also designed to provide fixation without the need for additional pins, screws, wires, or bone grafting. The plate is also designed for use with a targeting device to permit attachment to the bone without risking adjacent neurovascular structures. The design of the present bone buttress plate, thus, solves the problems of the prior art and meets the objects of the invention.

The invention further includes a surgical method of fixating a fractured calcaneus exposed in a surgical theater, which includes providing a bone buttress plate including a main body, a first and a second leg, and an extension member. Each leg attaches to and extends from the main body. The extension member includes a yoke, a first arm, and a second arm. The yoke attaches to the main body and extends from the main body opposite to the legs. Each arm attaches to and extends from the yoke.

The method then includes shaping the plate from a substantially planar configuration to an extent required for conformity to a lateral surface of the fractured calcaneus. The plate is then secured with mechanical fasteners to the fractured calcaneus, with each mechanical fastener retentionally engaged with the bone buttress plate and an underlying region of the fractured calcaneus.

The method may also include truncating the first arm and the second arm as necessary to fit a lateral surface of the fractured calcaneus.

The method may further include truncating the first leg and the second leg as necessary to fit the lateral surface of the fractured calcaneus.

The method may further include using a targeting device when establishing a attachment hole to accurately locate the hole and prevent damage to surrounding neurovascular structures.

BRIEF DESCRIPTION OF THE DRAWINGS

These and other features, aspects, and advantages of the present invention will become better understood with regard to the following description, appended claims, and accompanying drawings where:

DETAILED DESCRIPTION OF THE INVENTION

Figure 1:
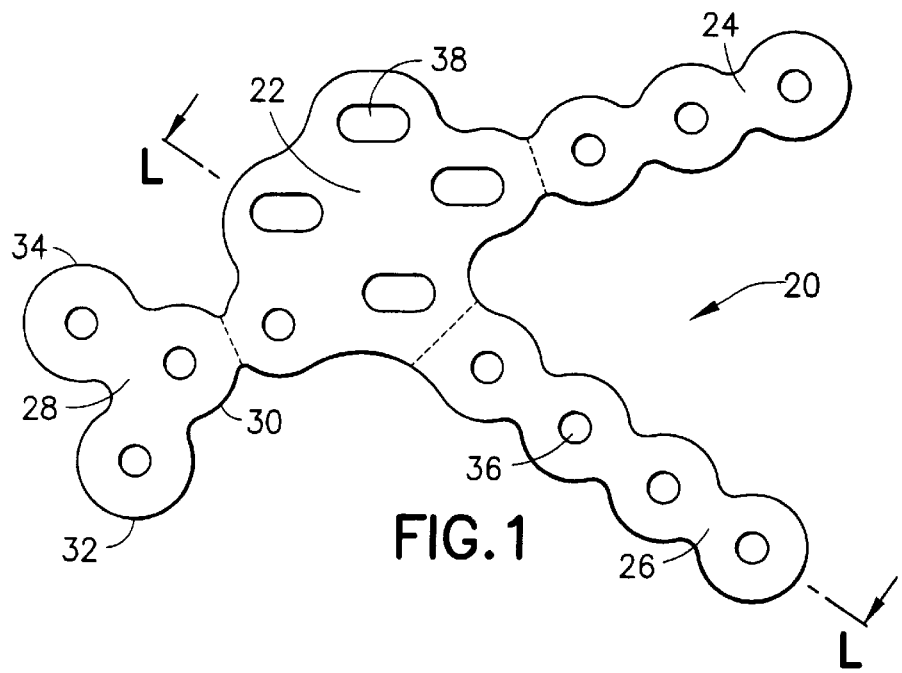
FIG. 1 is a plan view of a first embodiment of the present bone buttress plate invention.

FIG. 1 shows a bone buttress plate 20. Plate 20 comprises a main body 22, a first leg 24, a second leg 26, and an extension member 28. First leg 24 and second leg 26 each attach to and extend from main body 22. The extension member includes a yoke 30, a first arm 32, and a second arm 34. Yoke 30 attaches to main body 22 and extends from the main body generally opposite to first leg 24 and second leg 26. First arm 32 and second arm 34 are attached to and extend from yoke 30. The plate is shown with dotted lines demarcating the boundaries of the main body, each leg, the yoke, and each arm. Main body 22, legs 24 and 26, yoke 30, and arms 32 and 34 each include at least one opening 36 for attachment to a bone. Main body 22 further includes at least one generally oval opening 38 for attachment to the bone. Bone buttress plate 20 may preferably be formed of a thin malleable biocompatible material such as titanium or a titanium alloy.

Figure 2:
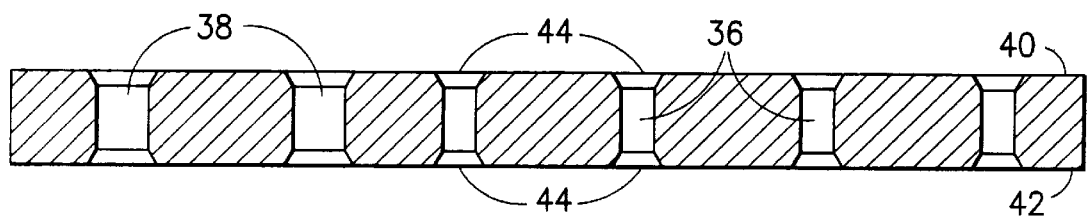
FIG. 2 is a sectional view of the bone buttress plate along line L—L of FIG. 1.

FIG. 2 shows an enlarged sectional view of plate 20 along line L—L of FIG. 1. Plate 20 includes a top surface 40 and a bone application surface 42. A countersink 44 is visible in each opening 36 and each generally oval opening 38. Countersinking is not necessary to practice the invention but is illustrated in the exemplary preferred embodiment.

Figure 3:
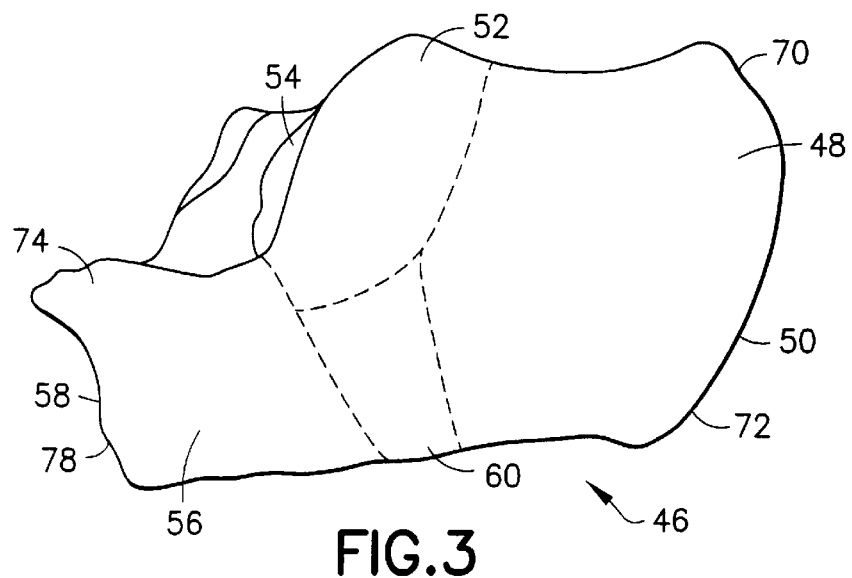
FIG. 3 shows the normal fracture pattern of the calcaneus lateral surface.

FIG. 3 shows the normal fracture pattern of a calcaneus lateral surface 46. Dotted lines denote lines of fracture and the boundaries of bone fragments. A large body fragment 48 contains the posterior tuberosity 50. A central fragment 52 normally contains a majority of the posterior articular facet 54. An anteromedial fragment 56 contains the anterior tuberosity 58. An intervening fragment 60 lies below central fragment 52 between large body fragment 48 and anteromedial fragment 56.

Figure 4:
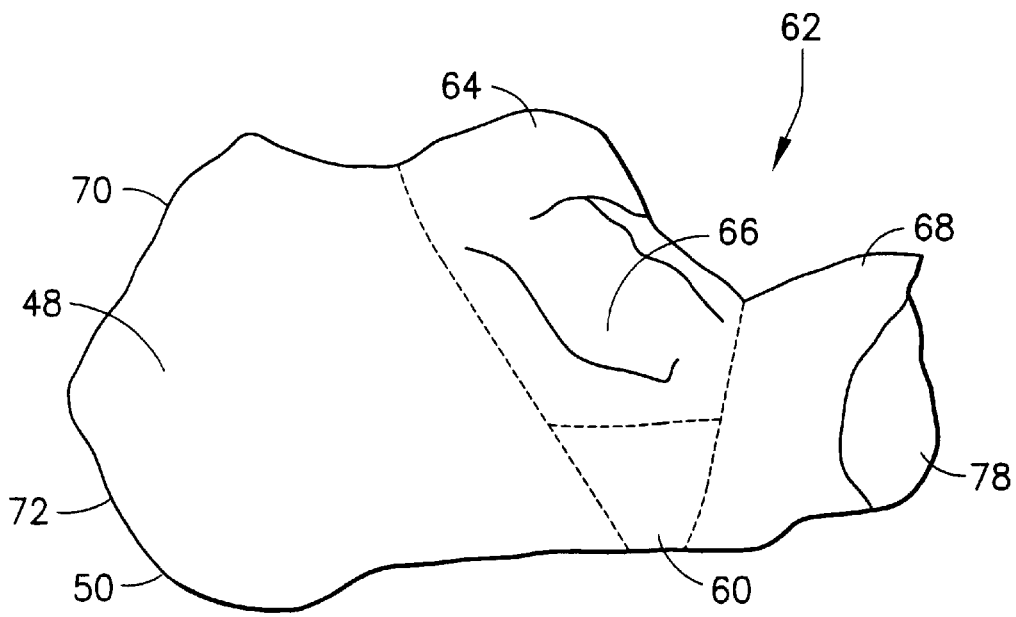
FIG. 4 shows the normal fracture pattern of the calcaneus medial surface.

FIG. 4 shows the normal fracture pattern of the calcaneus medial surface 62. Dotted lines again denote lines of fracture and the boundaries of bone fragments. Body fragment 48 lies posteriorly to a dense sustentacular fragment 64 containing the sustentaculum tali 66. Intervening fragment 60 again lies below the sustentacular fragment 64. In some cases the sustentacular fragment 64 can split forming an anterior articular facet fragment 68.

Figure 5:
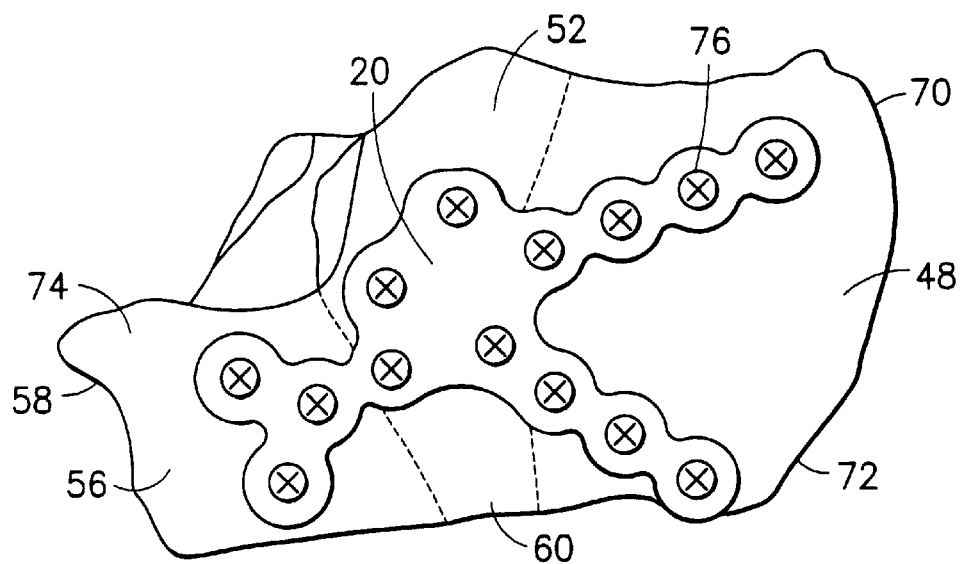
FIG. 5 shows the first embodiment of the present invention buttressing the lateral surface of a fractured calcaneus.

FIG. 5 shows an embodiment of the present invention buttressing the lateral surface of a severely fractured calcaneus. Plate 20 is positioned with legs, arms, and main body shaped to the contour of the calcaneus lateral wall. Plate 20 is positioned with first leg extending generally toward an upper third of the calcaneus posterior surface 70, second leg extending generally toward a lower third of the calcaneus posterior surface 72, first arm extending generally toward the anterior tuberosity 58, and second arm extending generally toward the great apophysis 74 of the calcaneus lateral surface. Mechanical fasteners 76 secure the anteromedial fragment 56 to the first and second arms. The mechanical fasteners in the anteromedial fragment 56 are driven generally parallel to the calcaneocuboid joint. Large body fragment 48 is secured to the legs by mechanical fasteners anchoring into body fragment 48.

Figure 6:
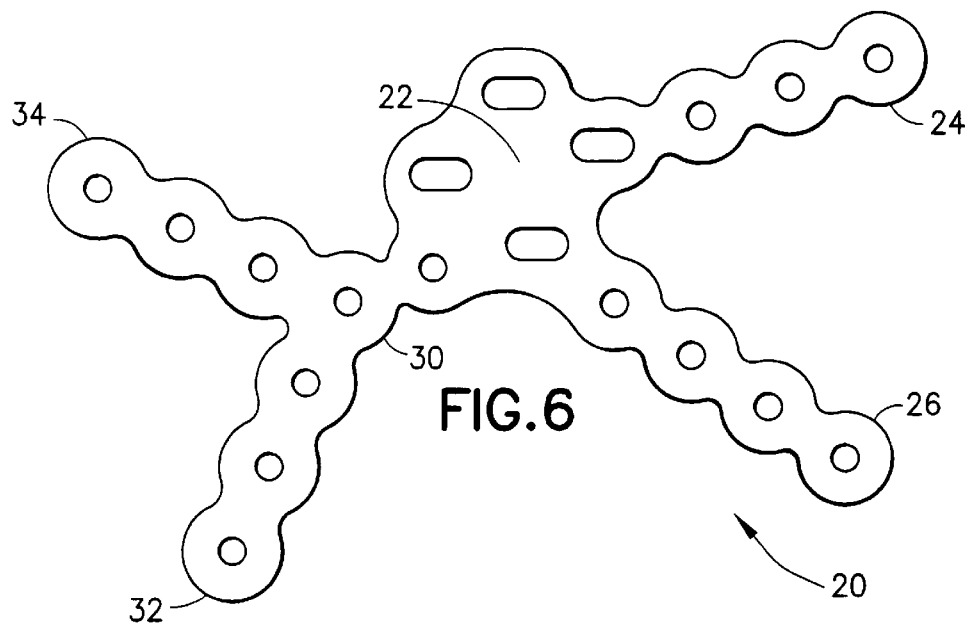
FIG. 6 is a plan view of a second embodiment of the present invention.

FIG. 6 is a plan view of another embodiment of the present invention. Since the calcaneus can vary in size from patient to patient, plate 20 can be constructed with the lengths of arms 32 and 34 increased to accommodate various bone sizes.

Figure 7:
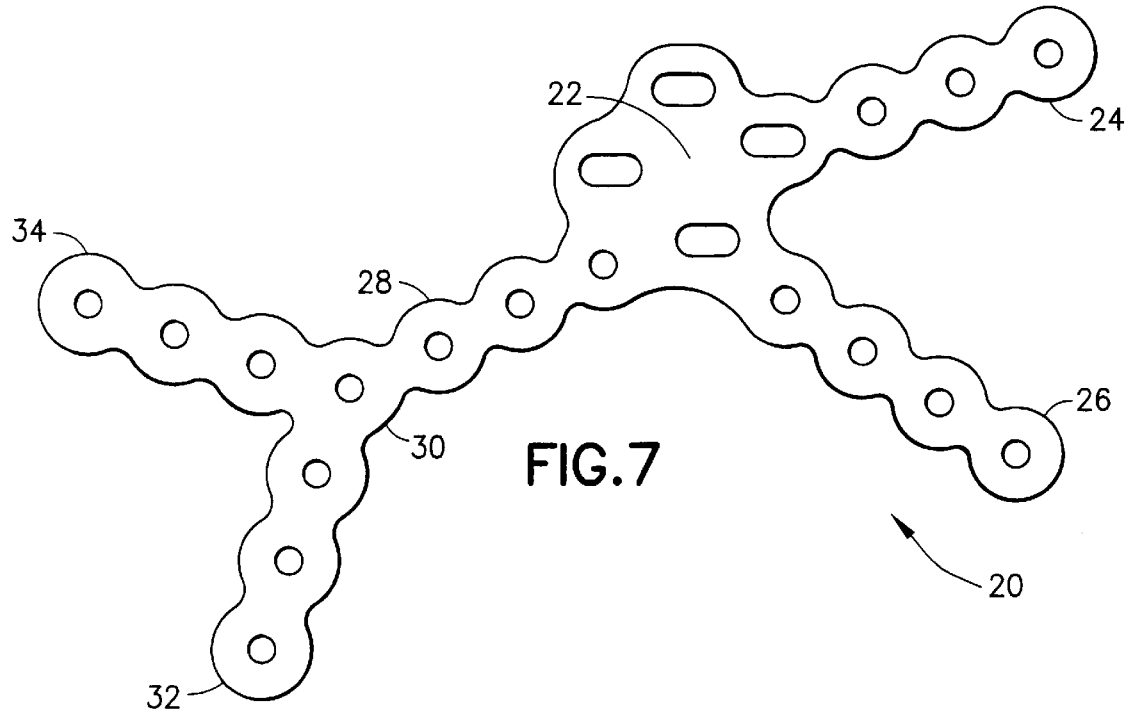
FIG. 7 is a plan view of a third embodiment of the present invention.

FIG. 7 is a plan view of another embodiment of the present invention. Plate 20 may also be constructed with the length of extension member 28 increased to accommodate various bone sizes.

Figure 8:
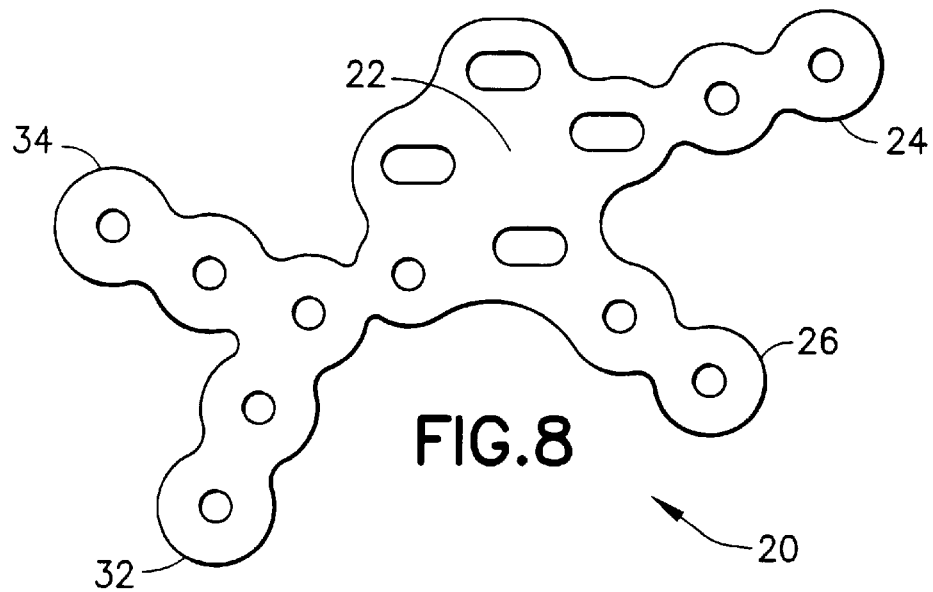
FIGS. 8 and 9 are plan views of the embodiments of FIGS. 6 and 7 respectively, with truncated arms and legs.
Figure 9:
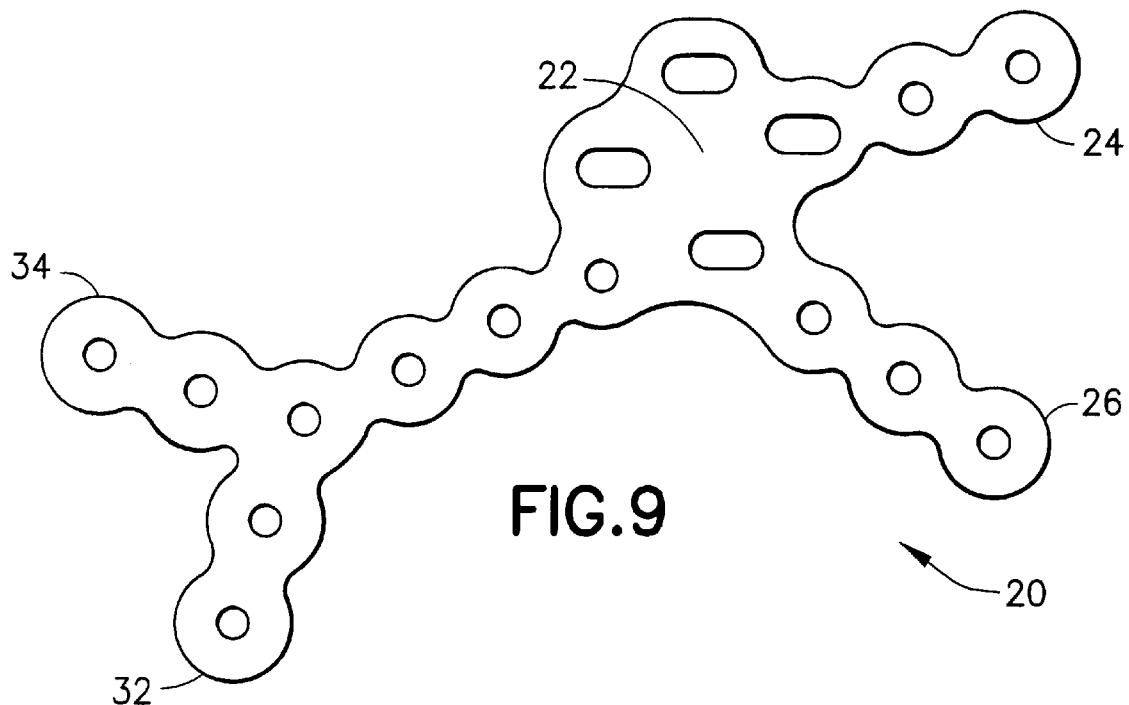

FIGS. 8 and 9 illustrate the ability to modify the arms and legs of the bone buttress plate 20 after manufacture to offer greater flexibility in accommodating various bone sizes. The lengths of first leg 24, second leg 26, first arm 32, and second arm 34 can be truncated by a technician, surgeon or other individual to fit a particular bone size. Modification can occur at the time of fixation surgery, at the time of x-ray diagnosis, during targeting or at any appropriate time. The design of plate 20 thus offers great flexibility in providing fixation for a wide variety of bone sizes. Modification can be accomplished with a simple cutting, bending or shearing tool.

The design of the plate ensures the large body fragment and the anteromedial fragment are each firmly secured at at least two points. The plate design bridges a severely comminuted region of a calcaneus lateral cortex, and the main body 22 firmly supports the mechanical fasteners entering into the central fragment 52 and anchoring into the sustentaculum fragment 64. A targeting device can be used to ensure the mechanical fasteners entering into the sustentacular fragment do not disturb the adjacent neurovascular structures.

Figure 10:
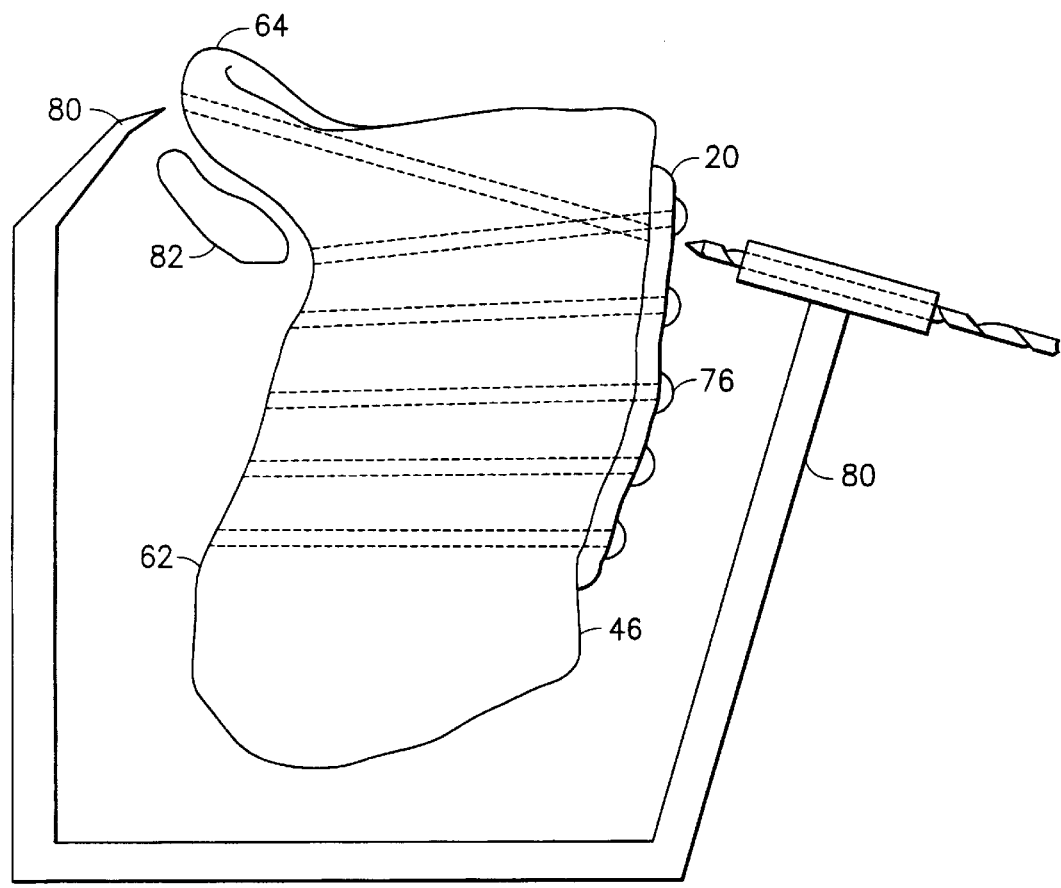
FIG. 10 shows an embodiment of the present invention used with a targeting device.

FIG. 10 shows an embodiment of the present invention used with a targeting device. The cancellous bone of the central calcaneus crushes under the pressure of the central fragment containing the posterior articular facet. The lack of solid bone in this vicinity forces the surgeon to blindly drill into the sustentaculum, and this procedure puts the flexor tendon and surrounding nerve, artery, and vein at risk. A targeting device 80 is used to establish drill holes into the sustentaculum and to prevent damage to surrounding neurovascular structures 82. Mechanical fasteners 76 can then safely secure the central fragment and anchor into the sustentacular fragment 64.

Figure 11:
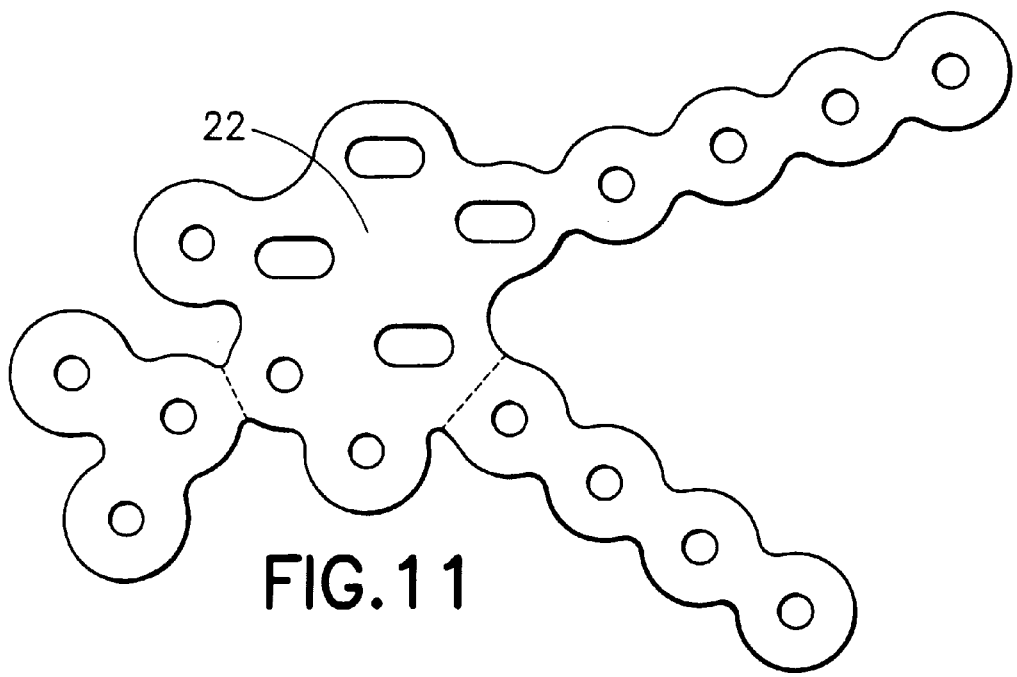
FIGS. 11 and 12 show embodiments of the present invention with differing main body shapes.

FIG. 11 shows an embodiment of the present invention with a generally cruciform shaped main body 22. The plate is shown with dotted lines demarcating the boundaries of the main body. The main body can be formed in the shape of a cross which offers convenient attachment points to bone fragments.

Figure 12:
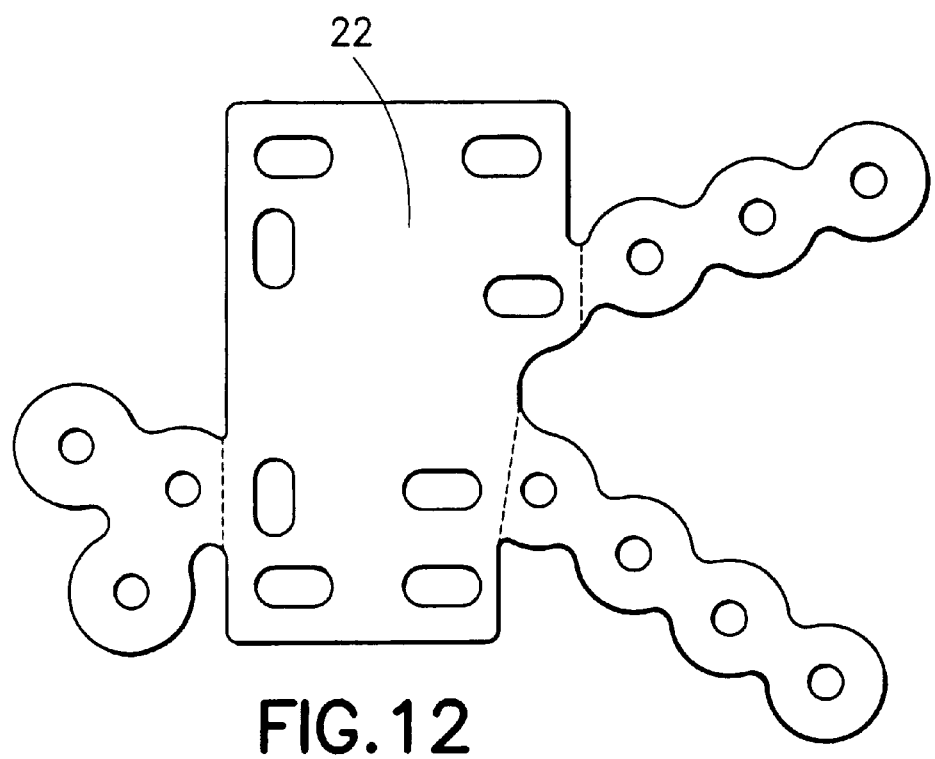

FIG. 12 shows an embodiment with a generally rectangular shaped main body 22. The plate is shown with dotted lines demarcating the boundaries of the main body. The rectangular shape of the main body allows the surgeon to customize the plate for fixating various bone fracture patterns.

The previously described embodiments of the present invention overcome the difficulties of past bone plate designs and meet all the objects of the invention. The main body 22 adds significant structure to the plate and prevents the plate from fracturing due to plantarward forces imparted on the plate during walking. The main body also bridges the severely comminuted calcaneus lateral cortex and provides a solid anchor for mechanical fasteners into the sustentacular fragment. The central fragment 52 is then properly supported without the need for additional pins, screws, or wires. Since the central fragment is adequately supported by the main body, the cancellous bone of the calcaneus can heal rapidly without the need of bone graft. The main body also allows a targeting device 80 to be used to safely establish mechanical fastener holes without risking the adjacent neurovascular structures.

The plate is also designed to improve fixation to the large body fragment 48 and to the anteromedial fragment 56. The first leg 24 and the second leg 26 provide at least two points of attachment to the body fragment, and each arm offers a plurality of openings 36 for anchoring mechanical fasteners. The first arm 32 and the second arm 34 also provide at least two points of attachment to the anteromedial fragment. These double attachment regions improve fixation to the body fragment and to the anteromedial fragment.

While the invention has been described herein with reference to specific embodiments and features, it will be appreciated the utility of the invention is not thus limited yet encompasses other variations, modifications, and alternative embodiments, and accordingly the invention is therefore to be broadly construed as comprehending all such alternative variations, modifications, and other embodiments within its spirit and scope.

What is claimed is:

1. A bone buttress plate consisting essentially of:
   (a) a main hub body having at least two openings, each such opening accommodating the passage of at least one mechanical fastener therethrough;
   (b) first and second legs attached to and extending from the main hub body wherein:
      i) each of the first and second legs has at least one opening;
      ii) each opening accommodates the passage of at least one mechanical fastener therethrough; and
      iii) the first and second legs form an angle which is less than 60°; and
   (c) an extension member attached to and extending from the main hub body from a location which is generally opposite to the legs and having at least one opening therein accommodating the passage of at least one mechanical fastener therethrough.

2. The bone buttress plate of claim 1 wherein:
   (a) the extension member is generally Y-shaped, comprising a leg and two arms;
   (b) the leg of the extension member is attached to the main hub body and extends from the main hub body at a position which is generally opposite to the first and second legs, and
   (c) the extension member has at least one opening in each arm accommodating the passage of at least one mechanical fastener therethrough.

3. The bone buttress plate of claim 1 wherein the extension member:
   (a) has a generally triangular shape having first, second and third angle regions; and
   (b) is attached to the main hub body at a first angle region of the generally triangular shape.

4. The bone buttress plate of claim 3 wherein the extension member has at least two openings positioned generally in the second and third angle regions of the generally triangular shape.

5. The bone buttress plate according to claim 1 wherein the openings in the main hub body include at least one generally oval opening for selectively adjustable positioning of an attachment means therein.

6. The bone buttress plate according to claim 1 wherein the main hub body has a shape selected from the group consisting of: generally cruciform; general circular, generally oval, generally square and generally rectangular.

7. The bone buttress plate according to claim 1 wherein the extension member has a length which is shorter than the lengths of each of the first and second legs.

8. The bone buttress plate according to claim 1 wherein the extension member has a length which is longer than the lengths of each of the first and second legs.

9. The bone buttress plate of claim 1 wherein the main hub body has at least three openings arranged in a non-linear pattern.

10. A bone buttress plate consisting essentially of:
   (a) a main hub body having at least two openings, each such opening accommodating the passage of at least one mechanical fastener therethrough;
   (b) first and second legs attached to and extending generally linearly from the main hub body wherein:
      i) each of the first and second legs has at least one opening; and
      ii) each opening accommodates the passage of at least one mechanical fastener therethrough; and
   (c) a generally Y-shaped extension member comprising a leg and two arms, wherein the leg is attached to and extends from the main body at a position which is generally opposite to the first and second legs, and wherein the extension member has at least one opening in each arm accommodating the passage of at least one mechanical fastener therethrough.

11. The bone buttress plate according to claim 10 wherein the openings in the main hub body include at least one generally oval opening for selectively adjustable positioning of an attachment means therein.

12. The bone buttress plate according to claim 10 wherein the main hub body has a shape selected from the group consisting of: generally cruciform; general circular, generally oval, generally square and generally rectangular.

13. The bone buttress plate of claim 10 wherein the extension member is attached to the main hub body at a location which is generally opposite to and with one of said legs.

14. The bone buttress plate of claim 10 wherein the first and second legs form an angle which is less than 60°.

15. The bone buttress plate of claim 10 wherein the extension member has a length which is shorter than the respective lengths of the first and second legs.

16. The bone buttress plate of claim 10 wherein the main hub body has at least three openings arranged in a non-linear pattern.

17. A bone buttress plate consisting essentially of:
   (a) a main hub body having at least two openings, wherein
      i) each such opening accommodates the passage of at least one mechanical fastener therethrough; and
      ii) at least one of such openings is generally oval shaped;
   (b) first and second legs attached to and extending from the main hub body wherein:
      i) each of the first and second legs has at least one opening; and
      ii) each opening accommodates the passage of at least one mechanical fastener therethrough; and
   (c) an extension member attached to the main hub body and extending therefrom at a position which is generally opposite to the first and second legs, the extension member having at least one opening accommodating the passage of at least one mechanical fastener therethrough.

18. The bone buttress plate of claim 17 wherein:
   (a) the extension member is generally Y-shaped, comprising a leg and two arms;
   (b) the leg of the extension member is attached to the main hub body and extends from the main hub body at a position which is generally opposite to the first and second legs, and
   (c) the extension member has at least one opening in each arm accommodating the passage of at least one mechanical fastener therethrough.

19. The bone buttress plate of claim 17 wherein the extension member:
   (a) has a generally triangular shape having first, second and third angle regions; and
   (b) is attached to the main hub body at a first angle region of the generally triangular shape.

20. The bone buttress plate of claim 19 wherein the extension member has at least two openings positioned generally in the second and third angle regions of the generally triangular shape.

21. The bone buttress plate according to claim 17 wherein the openings in the main hub body include at least two generally oval openings for selectively adjustable positioning of an attachment means therein.

22. The bone buttress plate according to claim 17 wherein the main hub body has a shape selected from the group consisting of: generally cruciform; general circular, generally oval, generally square and generally rectangular.

23. The bone buttress plate according to claim 17 wherein the first and second legs form an angle which is less than 60°.

24. The bone buttress plate of claim 17 wherein the extension member has a length which is shorter than the respective lengths of the first and second legs.

25. The bone buttress plate of claim 17 wherein the main hub body has at least three openings arranged in a non-linear pattern.

26. A bone buttress plate consisting essentially of:
   (a) a main hub body having at least two openings for attachment to a central fragment of a fractured calcaneus, wherein:
      i) each such opening accommodates the passage of at least one mechanical fastener therethrough; and
      ii) at least one of such openings is generally oval shaped;
   (b) two or more extension means extending from the main hub body such that when the main hub body is attached to the central fragment, at least one extension means is attachable to a calcaneus posterior surface and at least one extension means is attachable to an anteromedial fragment of the fractured calcaneus.

27. The bone buttress plate of claim 26 wherein the extension means are each attachable by at least one opening accommodating the passage of at least one mechanical fastener therethrough.

28. The bone buttress plate of claim 26 configured such that when the main hub body is attached to the central fragment:
   (a) at least one extension member can be attached at two points to a large body fragment of the fractured calcaneus; and
   (b) at least one extension member can be attached at two points to an anteromedial fragment of the fractured calcaneus.

29. The bone buttress plate of claim 26 wherein the main body of the plate, when fastened to the central fragment of the fractured calcaneus, bridges a comminuted region of a calcaneus lateral cortex of the fractured calcaneus.

30. The bone buttress plate of claim 26 wherein:
    (a) at least one extension means comprises a generally Y-shaped extension member, comprising a leg and two arms;
    (b) the leg of the extension member is attached to and extends from the main hub body;
    (c) the arms of the extension member are attached to and extend from the extension member at a position on the extension member which is opposite to the point of attachment of the extension member to the main hub body; and
    (d) the extension member has at least one opening in each arm accommodating the passage of at least one mechanical fastener therethrough.

31. The bone buttress plate of claim 30 wherein the extension member is generally Y-shaped.

32. The bone buttress plate of claim 26 wherein at least one extension means:
    (a) has a generally triangular shape having first, second and third angle regions; and
    (b) is attached to the main hub body at a first angle region of the generally triangular shape.

33. The bone buttress plate of claim 32 wherein the extension means has at least two openings positioned generally in the second and third angle regions of the generally triangular shape.

34. The bone buttress plate of claim 26 wherein the main hub body has a shape selected from the group consisting of: generally cruciform; general circular, generally oval, generally square and generally rectangular.

35. The bone buttress plate of claim 26 wherein the extension means comprises first and second legs attached to and extending from the main hub body wherein:
    (a) each of the first and second legs has at least one opening; and
    (b) each opening accommodates the passage of at least one mechanical fastener therethrough.

36. The bone buttress plate of claim 35 wherein the first and second legs form an angle which is less than 60°.

37. The bone buttress plate of claim 35 wherein the first and second legs each have a generally linear conformation.

38. The bone buttress plate of claim 37 wherein the main hub body has at least three openings arranged in a non-linear pattern.

39. A bone buttress plate consisting essentially of:
    (a) a main hub body having at least two openings, wherein
        i) each such opening accommodates the passage of at least one mechanical fastener therethrough; and
        ii) at least one of such openings is generally oval shaped;
    (b) first and second legs attached to and extending from the main hub body wherein:
        i) each of the first and second legs has at least one opening; and
        ii) each opening accommodates the passage of at least one mechanical fastener therethrough; and
    (c) an extension member comprising a leg and two arms, wherein:
        i) the leg of the extension member is attached to the main hub body and extends therefrom at a position which is generally opposite to the first and second legs; and
        ii) the extension member has at least one opening in each arm accommodating the passage of at least one mechanical fastener therethrough.

40. A bone buttress plate consisting essentially of:
    (a) a generally cruciform shaped main hub body having at least two openings, wherein each such opening accommodates the passage of at least one mechanical fastener therethrough;
    (b) first and second legs attached to and extending from the main hub body wherein:
        i) each of the first and second legs has at least one opening; and
        ii) each opening accommodates the passage of at least one mechanical fastener therethrough; and
    (c) an extension member comprising a leg and two arms, wherein:
        i) the leg of the extension member is attached to the main hub body and extends therefrom at a position which is generally opposite to the first and second legs; and
        ii) the extension member has a plurality of openings therein, each opening accommodating the passage of at least one mechanical fastener therethrough.

41. A bone buttress plate consisting essentially of:
    (a) a main hub body having a plurality openings, each such opening accommodating the passage of at least one mechanical fastener therethrough;
    (b) first and second legs attached to and extending from the main hub body wherein each of the legs is extended in length and is provided with a plurality of bone attachment openings to allow for truncation of any of said legs without loss of bone attachment capacity;
    (c) an extension member comprising a leg and two arms, wherein:
        i) the leg of the extension member is extended in length and is attached to the main hub body and extends therefrom at a position which is generally opposite to the first and second legs; and
        ii) the extension member has a plurality of openings therein to allow for truncation of said extension member without loss of bone attachment capacity, each opening accommodating the passage of at least one mechanical fastener therethrough.

42. A bone buttress plate consisting essentially of:
    (a) a main hub body having at least two openings, wherein each such opening accommodates the passage of at least one mechanical fastener therethrough;
    (b) first and second legs attached to and extending from the main hub body wherein:
        i) each of the first and second legs has at least one opening;
        ii) each opening accommodates the passage of at least one mechanical fastener therethrough; and
        iii) the legs together with the lateral extremity of the main hub body to which they are attached have a generally V-shape; and
    (c) a generally Y-shaped extension member comprising a leg and two arms, wherein:
        i) the leg of the extension member is attached to the main hub body and extends therefrom at a position which is generally opposite to the first and second legs and is generally aligned with one of the first and second legs; and
        ii) the extension member has a plurality of openings therein, each opening accommodating the passage of at least one mechanical fastener therethrough.

43. A method of fixating a fractured calcaneus comprising:
   (a) providing a bone buttress plate comprising:
      i) a main hub body having at least two openings for attachment to a central fragment of a fractured calcaneus, wherein each such opening accommodates the passage of at least one mechanical fastener therethrough; and
      ii) two or more extension means extending from the main hub body such that when the main hub body is attached to the central fragment, the extension means are attachable to a large body fragment of the fractured calcaneus and to an anteromedial fragment of the fractured calcaneus;
   (b) securing the main hub body of the plate with mechanical fasteners extending through the calcaneus lateral cortex to the sustentaculum; and
   (c) securing the extension means to the large body fragment and to the anteromedial fragment.

44. A calcaneous bone buttress plate for buttressing the lateral surface of a fractured calcaneous comprising a large body fragment, a central fragment, an anteromedial fragment, an intervening fragment, a body fragment lying posterior to a dense sustentacular fragment containing a sustentactulum tali, and optionally comprising an anterior articular facet fragment, said buttress plate consisting essentially of:
   (a) a main hub body having at least two openings, each such opening accommodating the passage of at least one mechanical fastener therethrough;
   (b) first and second legs attached to and extending from the main hub body wherein:
      i) each of the first and second legs has at least one opening;
      ii) each opening accommodates the passage of at least one mechanical fastener therethrough; and
      iii) the first and second legs form an angle which is less than 60°; and
   (c) an extension member attached to and extending from the main hub body from a location which is generally opposite to the legs and having at least one opening therein accommodating the passage of at least one mechanical fastener therethrough;

wherein the bone buttress plate is arranged in relation to the fractured calcaneous such that the first leg extends generally toward an upper third of the calcaneous posterior surface and can be secured thereto by mechanical fastener(s) extending through at least two of the openings of the first leg;

wherein the second leg extends generally toward a lower third of the calcaneous posterior surface and can be secured thereto by mechanical fastener(s) extending through at least two of the openings of the first leg;

wherein the legs are positioned in relation to the hub body such that when the first leg is attached to an upper third of the calcaneous posterior surface, and the second leg is attached to a lower third of the calcaneous posterior surface, the hub body supports mechanical fasteners entering through the openings of the hub body into the central fragment and anchoring into the sustentaculum fragment; and wherein the extension member is arranged in relation to the hub body such that when the first leg is attached to an upper third of the calcaneous posterior surface, and the second leg is attached to a lower third of the calcaneous posterior surface, and when the hub is attached to the central fragment, the extension member extends generally towards the anterior tuberosity and the great apophysis.

* * * * *

UNITED STATES PATENT AND TRADEMARK OFFICE
CERTIFICATE OF CORRECTION

PATENT NO. : 6,123,709
DATED : September 26, 2000
INVENTOR(S) : Andrew R. Jones

It is certified that error appears in the above-identified patent and that said Letters Patent is hereby corrected as shown below:

Column 1,
Line 9, change "intra-particular" to -- intra-articular --

Signed and Sealed this

Twelfth Day of October, 2004

JON W. DUDAS
*Director of the United States Patent and Trademark Office*